United States Patent [19]

McElroy et al.

[11] Patent Number: 5,118,398
[45] Date of Patent: Jun. 2, 1992

[54] METHOD AND AN APPARATUS FOR DETECTING IONIZABLE SUBSTANCE

[75] Inventors: James F. McElroy; William Smith, both of Suffield, Conn.

[73] Assignee: United Technologies Corporation, Hartford, Conn.

[21] Appl. No.: 446,031

[22] Filed: Dec. 5, 1989

[51] Int. Cl.$^5$ .................. G01N 27/26; G01N 27/40; G01N 27/406

[52] U.S. Cl. .................. 204/153.1; 204/153.13; 204/153.15; 204/153.16; 204/153.18; 204/409; 204/410; 204/421; 204/424; 204/431

[58] Field of Search ............... 204/409, 410, 421, 431, 204/432, 406, 153.1, 153.13, 153.15, 153.16, 153.18, 424, 427

[56] References Cited

U.S. PATENT DOCUMENTS

| 3,864,226 | 2/1975 | Spitzer | 204/98 |
|---|---|---|---|
| 4,030,988 | 6/1977 | Grot | 204/98 |
| 4,085,071 | 4/1978 | Resnick et al. | 204/98 |
| 4,123,700 | 10/1978 | La Conti et al. | 324/29 |
| 4,171,253 | 10/1979 | Nolan et al. | 204/195 S |
| 4,227,984 | 10/1980 | Demsey et al. | 204/195 S |
| 4,527,153 | 7/1985 | Suzuki et al. | 340/572 |
| 4,582,657 | 4/1986 | Shibata et al. | 264/40.6 |
| 4,657,659 | 4/1987 | Mase et al. | 204/410 |
| 4,718,991 | 1/1988 | Yamazoe et al. | 204/1 T |
| 4,795,533 | 1/1989 | Young et al. | 204/1 T |
| 4,797,190 | 1/1989 | Peck | 204/296 |
| 4,820,386 | 4/1989 | LaConti et al. | 204/1 T |

OTHER PUBLICATIONS

Hopfinger et al., "Prediction of the Molecular Structure of Nafion under Different Physiochemical Conditions", paper presented at the Electrochemical Society Meeting, Oct., 1977, 6 pages.

Yeo et al., *J. of Applied Electrochemistry*, "An Electrochemiclly Regenerative Hydrogen-Chlorine Energy System: Electrode Kinetics and Cell Performance", vol. 10 (1980, pp. 393-404.

Oronzio de nora, Impianti Elettrochimici, S.p.A. Milano; Electrolysis of HCl Solutions; dated Oct. 7, 1976.

James F. McElroy, U.S. Application Serial No. 07/328,279 entitled Electrochemical Hydrogen Separator System for Zero Gravity Water Electrolysis. Filed Mar. 24, 1989, Assignee: United Technologies Corporation.

Primary Examiner—T. Tung
Attorney, Agent, or Firm—Pamela J. Curbelo

[57] ABSTRACT

The amount of ionizable substance within a stream can be continuously monitored through the use of an ionizable substance detector. The substance is ionized at an electrode producing ions and free electrons. The ions are transported across an ion exchange membrane, while the free electrons flow through a power source. The current, produced by the electrons, is proportional to the amount of substance in the stream. Continuous monitoring can be useful in early detection of problems, or system fluctuations.

10 Claims, 1 Drawing Sheet

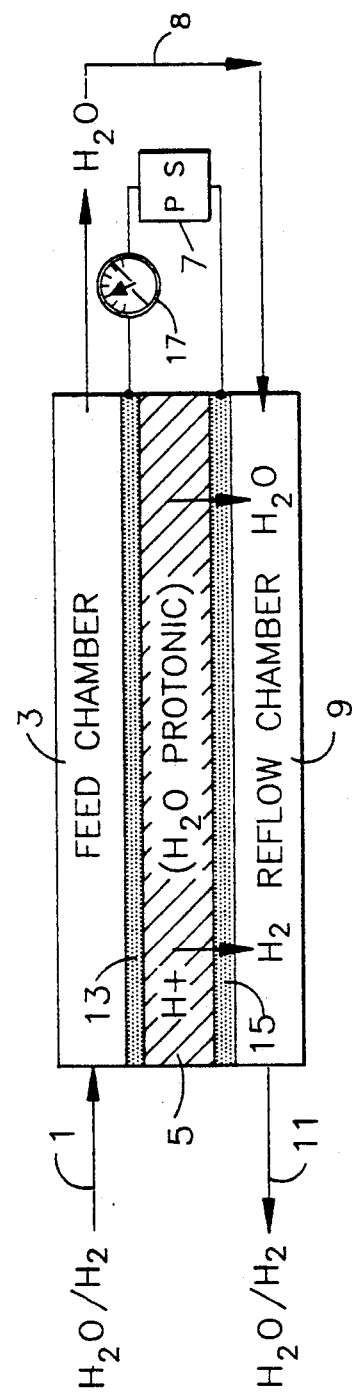

METHOD AND AN APPARATUS FOR DETECTING IONIZABLE SUBSTANCE

The invention described herein was made in the performance of work under NASA Contract No. NAS8-5000 and is subject to the provisions of Section 305 of the National Aeronautics and Space Act of 1958.

IONIZABLE SUBSTANCE DETECTOR

1. Technical Field

This invention relates to detecting ionizable substances, and especially to detecting ion forming substances

2. Background Art

Detecting ionizable substances, such as hydrogen, sodium, and chlorine, among others, within a stream can be important for various reasons. For example, within a fuel cell, electrolyzer, or other process, the amount of ionizable substance in a stream can be critical depending on the stream's use. A water stream for instance, intended for introduction into an oxygen stream, must be essentially free of hydrogen in order to prevent an explosion. In another instance, it may be necessary to monitor an exhaust stream to comply with environmental protection requirements U.S. Pat. No. 4,227,984 discloses a technique for sensing protons utilizing reference, sensing, and counter electrodes in combination with a membrane. All of the electrodes are located on one side of the membrane and positioned such that an ionic resistance path between the sensing and reference electrode is greater than 60 ohms. The arrangement places the reference electrode outside the current flux lines between the sensing and counter electrodes Similar techniques are disclosed in U.S. Pat. Nos. 4,123,700 and 4,171,253. Problems with these systems include a relatively slow response time (100 to 200 seconds), and a potential interference caused by permeation to the sensing electrode of the reactant products generated at the counter electrode U.S. Pat. No. 4,820,386 which discloses an improved method from that mentioned above resolves these problems Instead of locating all of the electrodes on one side of the membrane, the sensing and counter electrodes are located on the same side of the membrane with the reference electrode located on the opposite side of the membrane directly across from the sensing electrode. This arrangement allows for a faster, but still not sufficient, response time (approximately 12.0 seconds), with greater immunity to interference from counter electrode reaction products. Oxidation occurs at the sensing electrode and protons are transferred across the membrane by proton exchange between the sensing and counter electrode. The current generated is proportional to the partial pressure of the reactant gas in the stream.

Another method for sensing hydrogen (or carbon monoxide) is disclosed in U.S. Pat. No. 4,718,991. In this system, a pair of electrodes connected to a proton conductor are short-circuited to cause the protons to travel through the conductor. The potential difference produced in the interior of the conductor is obtained as the output of the sensor. The concentration of the hydrogen (or carbon monoxide) is proportional to this output. At the reference electrode, the hydrogen which has been ionized at the ionization electrode, is reacted with oxygen to form water. The disadvantages of this process include changing the composition of the stream (disturbing the stream), and the requirement of oxygen to operate the system.

Other techniques, such as removing, testing, and discarding samples from the stream or solution, have also been utilized for substance detection. However, in certain applications, such as extraterrestrial applications, this technique is not only impractical, it is inefficient and cumbersome.

The above mentioned devices have a potential for interference from the reaction products and operate relatively slow. What is needed in this art is a method for continually detecting the concentration of an ionizable substance within a stream in a relatively concise manner, without significantly disrupting the stream flow.

DISCLOSURE OF INVENTION

The present invention discloses a detector useful for continuously monitoring an ionizable substance in a fluid stream. The detector comprises a catalytic cathode and anode electrode, an ion exchange membrane, a power source, a current measuring device, and a means for introducing and removing the ionizable substance.

The method disclosed comprises applying a potential across the ion exchange membrane via a power source. The ionizable substance, ionized at the anode, produces ions and free electrons. The free electrons pass from the anode to the cathode through the power source. The amount of free electrons which pass through the power source, measured with a current measuring device, is proportional to the amount of the ionizable substance within the stream. The ions are then reformed into molecules at the cathode and removed from the detector.

The foregoing and other features and advantages of the present invention will become more apparent from the following description and accompanying drawings.

BRIEF DESCRIPTION OF DRAWINGS

The figure is a schematic of one embodiment of the present invention.

BEST MODE FOR CARRYING OUT THE INVENTION

The present invention can be utilized to detect any ionic substance, such as hydrogen, sodium, fluorine, chlorine, oxygen, bromine, among others, which, when ionized, produces free electrons. The Figure, a schematic of one embodiment of the present invention, reveals the essential aspects of the invention. The detector, possessing all of the conventional components of a fuel cell/electrolyzer, is comprised of an anode electrode (13), with a catalytic layer capable of ionizing the substance; a cathode electrode (15), with a catalytic layer, capable of recombining the ions and free electrons; and an ion exchange membrane (5) which is used as an ion transport medium disposed therebetween. A power source (7) is used to maintain a potential across the ion exchange membrane (5) to influence the flow of ions from the anode (13) to the cathode (15). The free electrons pass from the anode to the cathode through a current measuring device (17) which measures the amount of current produced by the flow of free electrons from the anode (13) to the cathode (15). In intimate contact with the anode is a means for introducing the substance (a feed chamber) (3), and, in intimate contact with the cathode is a means for removing the substance from the detector (a reflow chamber) (9).

In practicing the invention, the fluid stream (1) (such as a water stream, or a gas/gas stream) containing the ionizable substance enters the feed chamber (3). The substance is catalytically ionized at the anode electrode (13) producing ions and free electrons. A DC potential, maintained across the ion exchange membrane by the power source (7), influences the flow of ions across the ion exchange membrane (5) to the cathode (!5). The electrons simultaneously pass through the current measuring device (17) which monitors the current produced. At the cathode (15), the ions and electrons recombine to produce the molecular form of the substance. The molecular substance reenters the stream (1) which has simultaneously been passed through flow channel (8) and introduced to the reflow chamber (9). The stream (1) exits the detector at point (11).

The power source, which maintains the DC potential across the ion exchange membrane, serves two purposes: to conduct the free electrons produced at the anode electrode to the cathode electrode, and to supply the voltage necessary to influence the flow of ions from the anode to the cathode. Although any current measuring device which can accurately measure current can be utilized, an ampere meter is preferred. The current measured is proportional to the amount of ionizable substance present in the stream.

For example, for the detection of hydrogen in a water stream, each ampere of current flow removes 7.52 cc/min. of hydrogen from the stream. Therefore, the current which passes through the power source per unit time, is proportional to the amount of hydrogen detected. Knowing that 1 amp-min. is equivalent to pumping 7.52 cc of molecular hydrogen at any fixed voltage up to 1.23 volts (for this particular example), the amount of hydrogen within the stream can be determined. A voltage sufficient to transport the ions across the membrane without interfering with the current reading can be used.

In the particular application described above, a voltage of about 0.50 to about 1.23 volts is preferred, with 0.50 volts especially preferred. Voltages greater than 1.23 volts can cause water electrolysis which, in turn, affects the current reading and the accuracy of the detector.

Utilization of this invention with different substances may require a different type of catalyst and ion exchange membrane; both of which may be conventional. The type of catalyst will be dependent on the substance to be ionized, and the operating conditions. The ion exchange membrane will be dependent upon the size of the ionized substance, if it can be transferred across the membrane under a reasonable operating potential. Other factors which will affect the determination of the type of membrane to be utilized include the operating temperature, the type of ion to be transferred (cation or anion), and the chemical effects of the substance on the membrane and vice versa. All of these parameters can readily be determined by one skilled in this art.

In detecting hydrogen, for example, the catalyst must be capable of ionizing the hydrogen; and may be any one of a number of conventional catalysts utilized in electrolysis cells to disassociate hydrogen. The preferred catalyst is based on a metal from the platinum family, such as ruthenium, rhodium, palladium, iridium, and platinum, with platinum black bonded with Teflon ®, produced by Du Pont de Nemours, E. I. & Company, (metal loading of 4.0 mg/cm$^2$) especially preferred; although different catalysts can be utilized.

Various ion exchange membranes can also be utilized, with Nafion ® produced by Du Pont de Nemours, Inc., preferred. The operating temperature for Nafion should not exceed approximately 250° F. Therefore, any device utilizing this particular membrane preferably operated above the freezing point of the stream, and below approximately 250° F.

As with the temperature, the pressure and flow rates of the stream can vary greatly. In order to detect the substance at various temperatures, pressures, and flow rates, the output readings must be calibrated for the particular substance to be detected, and the system operating conditions.

To calibrate the system, the pressure, temperature, and flow rate are held constant for the desired conditions; while the stream containing the substance is passed through the detector. Once the stream exits the detector, it is placed within a conventional device for measuring the substance. Hydrogen, for example, can be placed within low pressure device which liberates the hydrogen, allowing the amount of hydrogen in the stream to be measured. The amount of substance determined by the detector is compared with the amount of substance actually in the stream. If, for instance, 72.0 percent of the substance was detected with the detector, the detector reading must be adjusted. The adjustment consists of dividing the amount of substance detected by 0.72 to determine the actual amount of substance within the stream.

This process, which permits continuous monitoring of the substance concentration within a fluid stream, creates detection devices for discovering problems, or system fluctuations early. Also, since the substance is reintroduced to the stream, the problem of disposing the test sample never arises, nor does the problem of accumulating test samples within the system; the stream is essentially undisturbed by the process. Furthermore, if the stream is homogeneous, this determination is highly accurate; without invasive sampling.

This invention is particularly useful for detecting hydrogen in a water stream of a fuel cell/electrolyzer system where it is necessary to have a closed system and/or where the hydrogen must not exceed a given maximum. For instance, where the water stream is intended for astronaut consumption, or where the water stream will be introduced to an oxygen stream, it can be important or even critical to keep the hydrogen content of the water to a minimum. Continous monitoring of the hydrogen concentration within the water stream will allow early detection of potential disasterous problems; enabling them to be avoided.

EXAMPLE 1

The following procedure can be utilized to detect hydrogen within a water/hydrogen stream for a life support system which produces approximately 9.08 pounds of oxygen per day. (refer to the Figure).

1. A water/hydrogen stream is introduced to the feed chamber (3) of the detector at 22.0 cc/min., 120° F., and 160 psia.
2. The hydrogen within the stream contacts a platinum black bonded with Teflon (metal loading of 4.0 mg/cm$^2$) catalyst at the anode electrode (13), and is catalytically ionized producing ions and free electrons.
3. The ions are transported across the Nafion ion exchange membrane to the cathode electrode (15)

under the influence of a DC potential maintained by the power source (0.50 volts).
4. The free electrons pass through the power source (7), and external electric circuit, to the cathode electrode (15). The current is monitored with an ampere meter (17). The reading is received in less than 1.0 second.
5. The ions and free electrons are recombined to form molecular hydrogen at the cathode electrode (15) where a platinum black bonded with Teflon (metal loading of 4.0 mg/cm$^2$) catalyst is present.
6. The molecular hydrogen is reintroduced into the stream, from which it was taken, in the reflow chamber (9). The reintroduction of the hydrogen into the stream prevents the detection operation from significantly disturbing the stream.

EXAMPLE 2

The following procedure can be utilized to detect hydrogen within the water stream of a hydrogen/oxygen system for producing rocket propulsion reactants. The operating parameters for this system are: 3,000 psi, 120° F., and the water/hydrogen flow is 106 cc/min (oxygen and hydrogen flow to the system are 1.78 lbs/hr, and 0.22 lbs/hr, respectively).

The parameters in Example 1 can be followed. Since the temperature of this system does not exceed 250° F., the ion exchange membrane is Nafion. Platinum black bonded with Teflon (metal loading of 4.0 mg/cm$^2$) catalyst is used at both electrodes.

Although this invention has been shown and described with respect to detailed embodiments thereof, it will be understood by those skilled in the art that various changes in form and detail thereof may be made without departing from the spirit and scope of the claimed invention.

We claim:

1. A method of detecting ionizable substance in a stream, which comprises:
   a. using a detector, said detector including a means for introducing and a means for removing said stream containing an ionizable substance, a current measuring device, a power source, a catalytic cathode electrode, a catalytic anode electrode, and an ion exchange membrane disposed therebetween;
   b. introducing said stream containing said ionizable substance to the anode electrode via said means for introducing said stream;
   c. applying and maintaining a potential across said ion exchange membrane from said power source;
   d. ionizing said substance at said anode electrode, wherein ions and free electrons are produced;
   e. transferring said ions across said ion exchange membrane to said cathode electrode;
   f. passing said free electrons through said power source to said cathode electrode;
   g. using said current measuring device to determine the current produced by the free electrons which pass through said power source, wherein said current measuring device is connected to said power source;
   h. recombining said ions and said free electrons at the cathode electrode to produce the molecular form of said ionizable substance; and
   i. reintroducing the molecular substance to said stream in said means for removing said stream, wherein said stream flows first through said means for introducing said stream and then through said means for removing said stream;
   whereby the current flow of the electrons across the power source is the same as the current flow of the ions across the ion exchange membrane, and wherein measurement of said current provides a measurement of the ionizable substance flow.

2. A method as in claim 1 wherein said ionizable substance is selected from the group which consists of hydrogen, sodium, fluorine, chlorine, oxygen, and bromine.

3. A method as in claim 1 wherein both of said catalytic anode and said catalytic cathode comprise a catalyst, and wherein said catalysts are based on a metal selected from the group consisting of ruthenium, rhodium, palladium, iridium, and platinum.

4. A method as in claim 1 wherein said current measuring device is an ampere meter.

5. A method as in claim 1 wherein said means for introducing and means for removing said stream comprises two chambers; whereby one chamber is one the anode electrode side of the ion exchange membrane, and the other chamber is on the cathode electrode side of the membrane.

6. Apparatus for detecting an ionizable substance in a stream comprising:
   a. a means for introducing said stream containing said ionizable substance to the apparatus, said means for introducing constructed and arranged for allowing said stream to exit to a flow channel;
   b. A catalytic anode electrode for ionizing said substance, producing ions and free electrons;
   c. A catalytic cathode electrode for recombining said ions with said free electrons to return said substance to its molecular form and to reintroduce the reformed substance back into said stream;
   d. anion exchange membrane for transporting said ions from said anode electrode to said cathode electrode, wherein said ion exchange membrane is disposed between and in intimate contact with said anode electrode and said cathode electrode;
   e. a power source for maintaining a potential across said ion exchange membrane and through which said free electrons pass, wherein said potential influences the flow of said ions from the anode electrode to the cathode electrode;
   f. a current measuring device connected to said power source, wherein said current measuring device monitors the amount of electrons which pass through said power source; and
   g. a means for removing said stream containing said reintroduced substance from said apparatus, wherein said means for removing is constructed and arranged for accepting said stream from the flow channel and said stream passes through said means for introducing, enters the flow channel, passes through the flow channel, and enters said means for removing such that said means for introducing and said means for removing are in flow communication;
   whereby the flow of the free electrons through the power source is proportional to the amount of ionizable substance within the stream.

7. An apparatus as in claim 6 wherein both of said catalytic anode and catalytic cathode comprise a catalyst, and wherein said catalysts are based on a metal selected from the group consisting of ruthenium, rhodium, palladium, iridium, and platinum.

8. An apparatus as in claim 6 wherein said current measuring device is an ampere meter.

9. An apparatus as in claim 6 wherein said means for introducing said stream is a chamber.

10. An apparatus as in claim 6 wherein said means for removing said stream is a chamber.

* * * * *